United States Patent
Shimoda

[11] Patent Number: 5,899,696
[45] Date of Patent: May 4, 1999

[54] DENTAL IMPLANT

[76] Inventor: Tsunehisa Shimoda, 8-40-1006, Jyosei 1-chome, Sawara-ku, Fukuoka-shi, Fukuoka, 814, Japan

[21] Appl. No.: 08/696,838
[22] PCT Filed: Dec. 26, 1995
[86] PCT No.: PCT/JP95/02694
  § 371 Date: Jan. 28, 1997
  § 102(e) Date: Jan. 28, 1997
[87] PCT Pub. No.: WO96/19949
  PCT Pub. Date: Jul. 4, 1996

[30] Foreign Application Priority Data

Dec. 28, 1994 [JP] Japan .................................. 6-338731

[51] Int. Cl.$^6$ ...................................................... A61C 8/00
[52] U.S. Cl. ............................................ 433/173; 433/172
[58] Field of Search .................................... 433/172, 173, 433/174, 175, 176, 201.1

[56] References Cited

U.S. PATENT DOCUMENTS 2,258,207 10/1941 Irwin ........................................ 433/176
4,359,318 11/1982 Gittleman ................................ 433/173
5,372,503 12/1994 Elia ......................................... 433/173

FOREIGN PATENT DOCUMENTS 2-200258 8/1990 Japan .
5145 1/1993 Japan .

Primary Examiner—John J. Wilson
Attorney, Agent, or Firm—Armstrong, Westerman, Hattori, McLeland & Naughton

[57] ABSTRACT

A dental implant is provided that can be firmly fixed in an oral cavity, even if the amount of bone required to embed the implant is small. A necessary amount of bone can be secured by generating new bone so that the fixture part of the implant can be fixed in the bone. The fixture part of the implant includes several members movably connected to each other so that the fixture part is adjustable in length. The fixture part includes a first member made up of an uppermost member, a middle member, and an end member. It is preferred that the middle member be cylindrical or rod-shaped with male screws extending radially outwardly from an outer circumferential periphery thereof. The fixture part also includes a second member which is a hollow cylinder. It is preferred that the hollow cylinder have a tapped hole on one end with female screw on an inner periphery thereof so that the middle member of the first member can be screwed into the second member. The continuous stimulating force formed by the embedment of the implant into bone and the lifting up of the mucous membrane by extending the fixture part of the implant, contributes to the osteogenesis around the implant.

12 Claims, 12 Drawing Sheets

DENTAL IMPLANT

TECHNICAL FIELD OF THE INVENTION

The present invention generally relates to a dental implant and more particularly, to an improved two part dental implant including a fixture part fixedly embedded into a bone, such as a mandible or maxilla, and an abutment part protruding outwardly from the bone into the dental cavity in order to fasten such dental protheses as dentures and cast crowns.

BACKGROUND OF THE INVENTION

It is well know that dental implants, having a fixture part which is to be embedded into bone and an abutment part which is to be mounted on the tip of the fixture part, are used to fix dental protheses such as dentures or cast crowns. Conventional implants have a wide variety of geometrical forms and lengths. Conventional implants also have a singular structure which is to be inserted or embedded into bone and conventional implants can be divided into the categories of submerged type structures and non-submerged type structures depending on the means of their embedment. An implant for a non-submerged type structure has an abutment which is exposed in the oral cavity, while an implant for a submerged type structure has no such embedment initially, but will receive an abutment to be mounted after a certain period of time has passed from the operation or surgery during which the implant is embedded.

Conventional implants require a substantial amount of bone in which to be inlaid. If there is not a sufficient amount of bone in which to embed the implants, for instance, such as in the case of vertical bony defects wherein upper and lower alveolar bones have become atrophied by age, the patients are compelled to give up on having dental therapy with implants, unless the required amount of bone is transplanted.

On the other hand, the Distraction Osteogenesis Theory, first described in 1988 by G. A. Ilizarov, a Russian medical doctor, has attracted public attention as a medical method applicable to the treatment of malformation or such therapy against abnormal bone length. This osteogenetic method has produced good results for over 35 years in the correction of the form of the bone and the soft tissue. Although this technique has not as of yet been applied to any vertical bone augmentation, it is considered to be applicable not only to the orthopedic field, but also to the stomatognathic field, for example, to the improvement of the length, width, and radius of the lower jaw. This method has also been experimentally studied in Japan.

The idea of an augmented amount of bone to recover the bony form against substantial bone defect, malformation and atrophy has great medical possibilities. That is, this idea is based on the unique Distraction Osteogenesis Theory, which is in turn based on the concept that the continuous stimulating force has osteogenetic power and the capacity of mucous membrane expansion.

On the other hand, such an idea as osteogenesis has never been conceived up to now in any clinical studies or research of dental implants. The implant body has thus far been embedded only into a given bone.

SUMMARY OF THE INVENTION

The object of the present invention is to provide a dental implant that can be firmly fixed into the oral cavity of the patient for securing or producing the amount of bone required for the embedment of the implant by applying the idea of distraction osteogenesis, even without performing a bone transplantation.

The above-described object of the present invention is attained by the dental implant having a fixture part and an abutment part, wherein the fixture part to be embedded in bone consists of plural members connected so as to be adjustable with respect to their effective length. More particularly, it is preferred that a rod-shaped, tapped middle member having a male screw be screwed into a cylindrical threaded exterior member having a female screw.

The fixture part of the implant of the present invention is embedded into bone such as a maxilla or mandible. The length of the fixture part may be extended at a suitable period of time after the operation or surgery to embed the fixture part in order to lift up the mucous membrane from the surface of the bone into a tent-like shape, thereby making the continuous stimulating force having either osteogenetic power or mucous membrane augmenting capacity act to guide the bone physiologically to the circumference of the implant in the cavity that was produced due to the mucous membrane being lifted. A required amount of bone is thus produced around the implant without any particular bone transplantation being necessary to firmly hold the implant. The present invention allows the production of the required amount of bone around the implant to hold the implant firmly, thus making use of the unique idea of distraction osteogenesis based on the concept that the continuous stimulating force has osteogenetic power and mucous membrane expanding capacity. The implant according to the present invention is therefore considered to be a landmark implant which is conceptually quite different from conventional implants.

DETAILED DESCRIPTION OF THE INVENTION

In the exemplary embodiments of the present invention as disclosed in the drawings, FIGS. 1–4 illustrate an implant for an upper jaw S as an first embodiment thereof. The implant for the upper jaw S has an exterior member 1 and a middle member 2 which are screwed into each other. The implant also includes an abutment 3, which can be mounted on the lower edge of the exterior member 1, and a healing cap 4.

Figure 2:
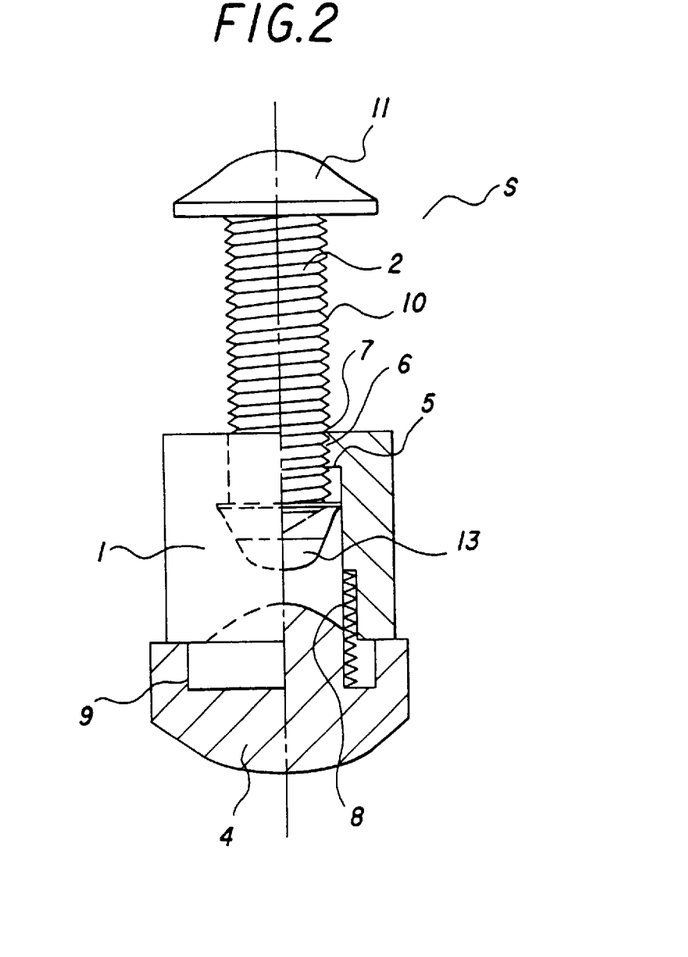
FIG. 2 is a partial longitudinal cross-sectional view detailing the right half of the dental implant of the first embodiment of the present invention, wherein the implant is for an upper jaw and wherein a middle member and a healing cap are shown as being screwed into first and second ends of an exterior member, respectively.
Figure 3:
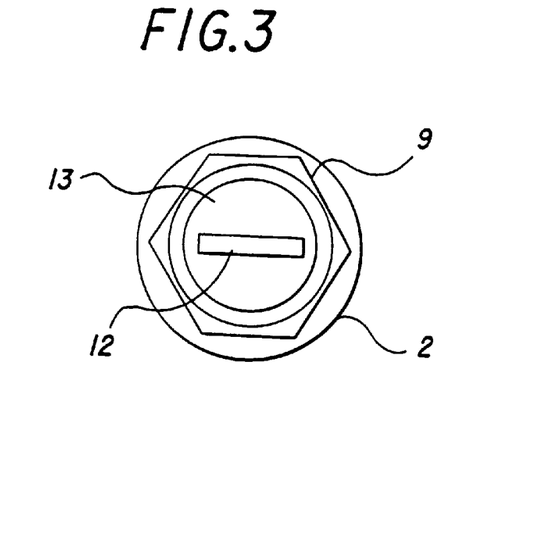
FIG. 3 is a bottom view of the dental implant of FIG. 2 showing the healing cap removed.
Figure 4:
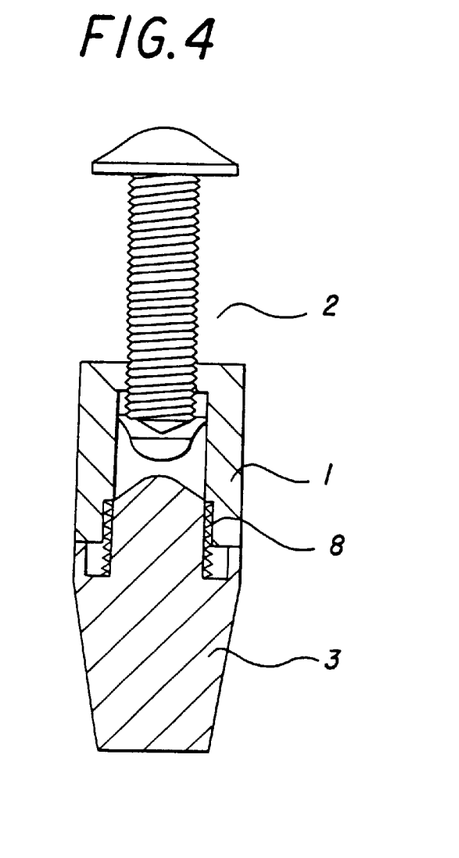
FIG. 4 is a longitudinal cross-sectional view of the dental implant of FIG. 2 showing an abutment mounted on the exterior member in place of the healing cap.

The exterior member 1 is formed into a cylinder that is open at a lower edge thereof and as seen by reference to the drawings, the exterior member has a hollow throughout. The exterior member 1 is provided with an inward flange 5 at an upper edge thereof. The inward flange 5 surrounds a central tapped hole 7 in the upper edge of the exterior member 1. The inwardly facing outer surfaces of the inward flange 5 have female screws 6 thereon. The lower inner circumference of the exterior member 1 is provided with a female screw portion 8 for screwing either the healing cap 4 or the abutment 3 thereinto. The lower edge of the exterior member 1 has a hexagonal nut 9.

Figure 1:
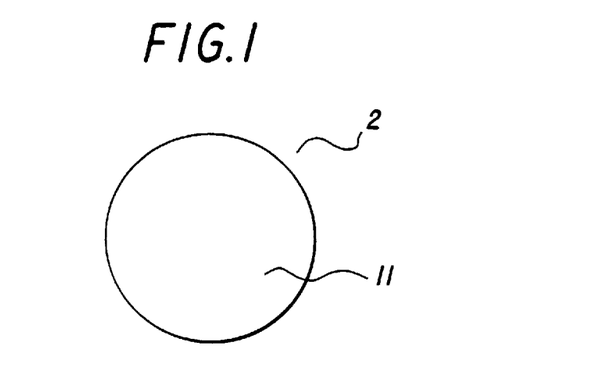
FIG. 1 is a plan view of the middle member of a dental implant according to a first embodiment of the present invention.

The middle member 2 has an uppermost member 11 at the top of the rod-like body of the middle member 2. The middle member 2 has an outer circumference which is threaded with a male screw 10. At the lower edge of the middle member 2, there is an end member 13 having a groove for engagement with a flat or cruciform screwdriver.

Figure 5:
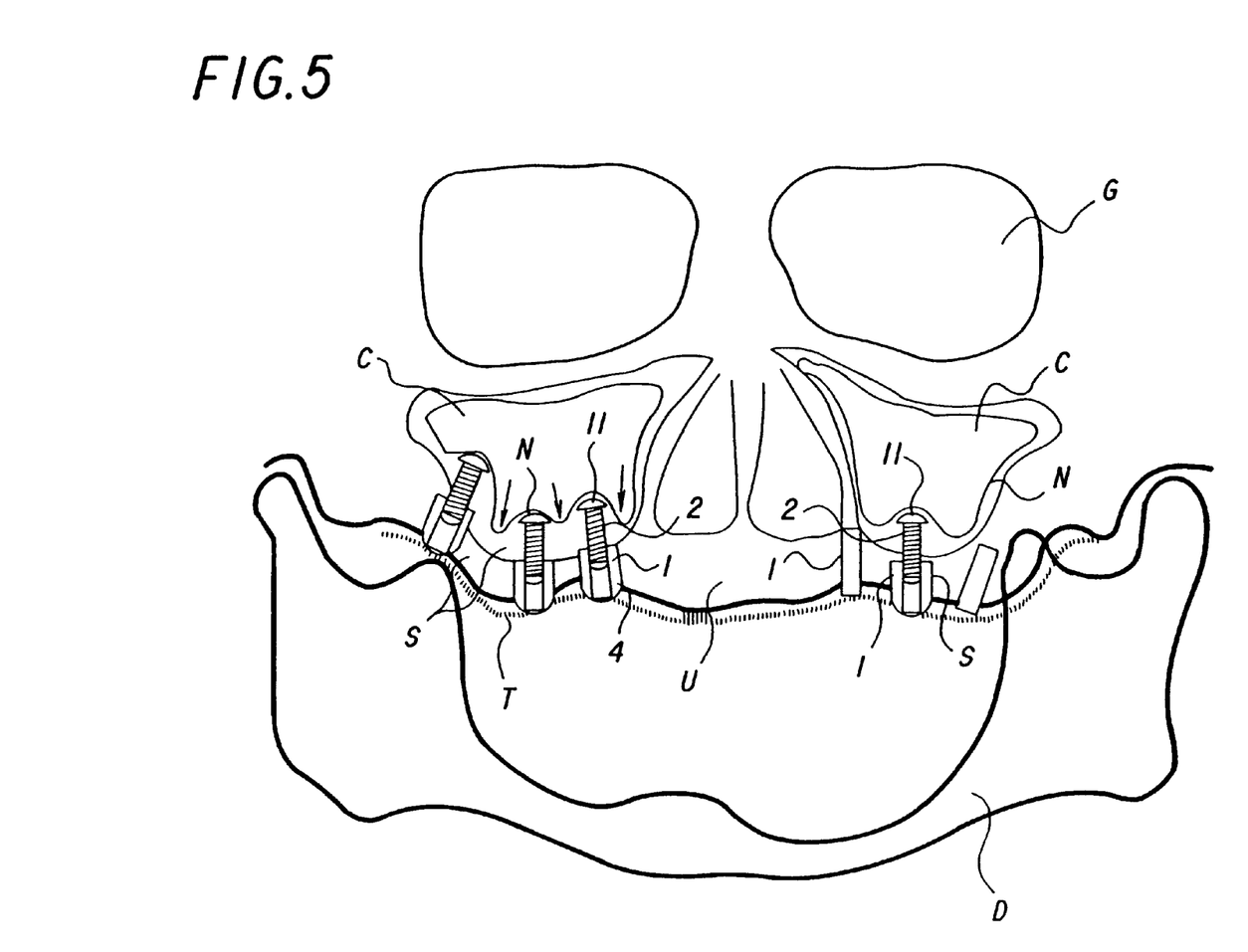
FIG. 5 is a schematic of a human skull showing the dental implants for an upper jaw of the first embodiment of the present invention in a state just after an operation or surgery wherein the implants were embedded into the patient's maxilla.

As shown in FIG. 5, the exterior member of the implant S for the upper jaw is inlaid into a human maxilla U from the oral cavity side, and the middle member 2, which is screwed into the exterior member 1, is turned by a screwdriver so that the uppermost member 11 thereof is projected upwardly. The healing cap 4 has been screwed into the lowermost portion of the exterior member 1. Thus, the uppermost member 11 of the middle member protrudes into the maxillary sinus C to lift up the mucous membrane N with the uppermost member 11 thereby producing a space or cavity between the mucous membrane N and the maxilla U.

Letter I in FIG. 5 represents a conventional implant, letter D represents the mandible of the human into which the implants are embedded, and letter G represents the eyeballs of the human into which the implants are to be embedded.

Letter T represents the mucous membrane on the inner face of the oral cavity of the human the implants are to be embedded into. During the operation or surgery in which the implants S are embedded, the mucous member N is incised to embed the implants S.

Figure 6:
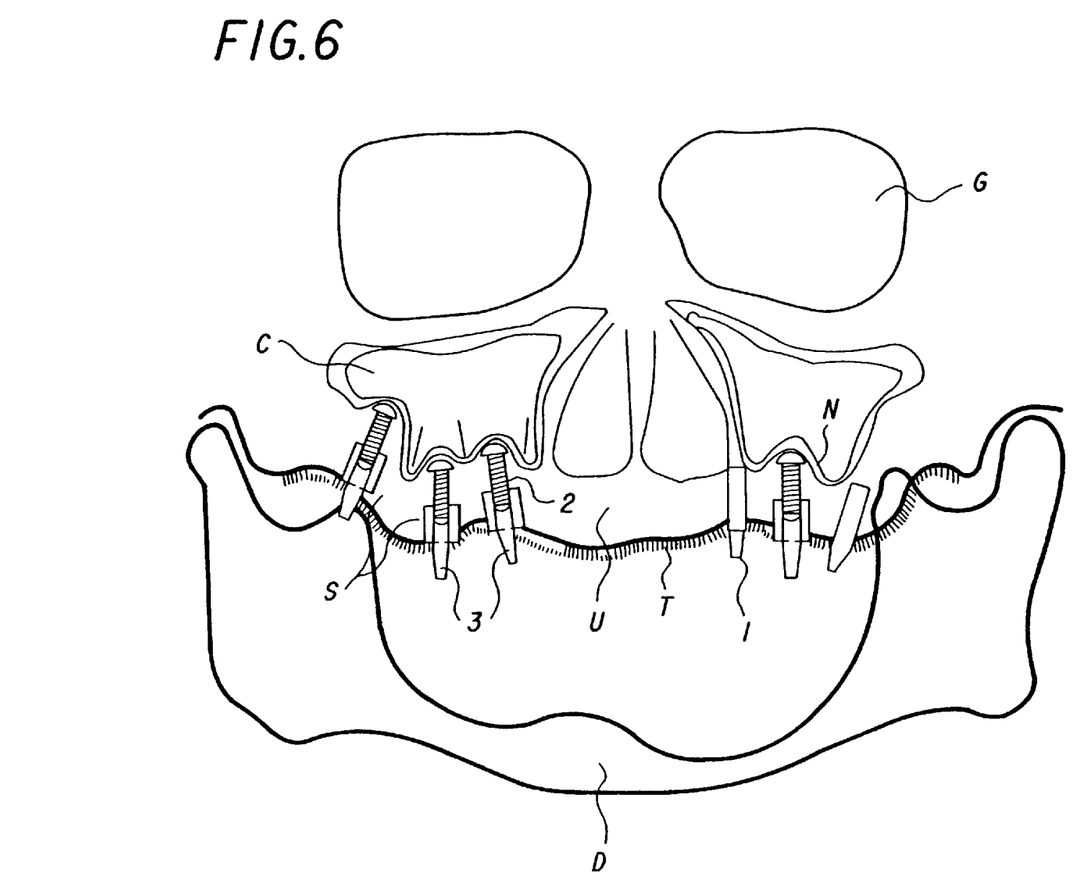
FIG. 6 is a schematic of a human skull illustrating how the same dental implants as in FIG. 5 would look six months after the operation or surgery.

If this state is left to stand for a suitable period of time, for example, six months after the operation or surgery to embed the implants S, a bone is formed in the cavity under the mucous membrane N which has been lifted into the interior of the maxillary sinus C with the middle member 2 of the implant embedded into the bone, thus firmly fastening the implant S as a whole. When the implant S is firmly fastened at a whole to the bone, the abutment 3 is screwed into the female screw portion 8 in the opening of the exterior member 1 so that the abutment 3 is exposed to the outside of the mucous membrane T in the oral cavity. Such protheses as dentures and cast crowns can be mounted by means of this abutment 3. Alternatively, welding may be adopted as a method for mounting the abutment 3.

Although the implant S belongs to the submerged type conventional classification, it is pathophysiologically and structurally different from the conventional implants, which seek the construction of the implant body, as developed, based on its maintenance in the bone, and which also seek the bone-affinity type strength of its materials. That is, the dental implant of the present invention has been so designed that the intrinsic maxillary sinus, in the maxilla with a relatively small amount of bone, is narrowed to induce the production of bone, based on the original ideal of the distraction osteogenesis, which in turn is based on the concept that the continuous stimulating force has bone producing power and mucous membrane augmenting capacity.

The dental implant of the present invention has a unique double structure which theoretically allows the effective length of the implant itself to be extended to about twice the initially embedded implant. The dental implant of the present invention also allows the middle member to lift up the mucous membrane of maxillary sinus in order to introduce bone therearound. From a structural point of view, the middle member plays the role of an anchor in the bone. Moreover, the dental implant of the present invention displays an excellent holding power, since it has a bicortical structure in which both the maxillary sinus side and the oral cavity side are surrounded by the cortical bone.

Figure 7:
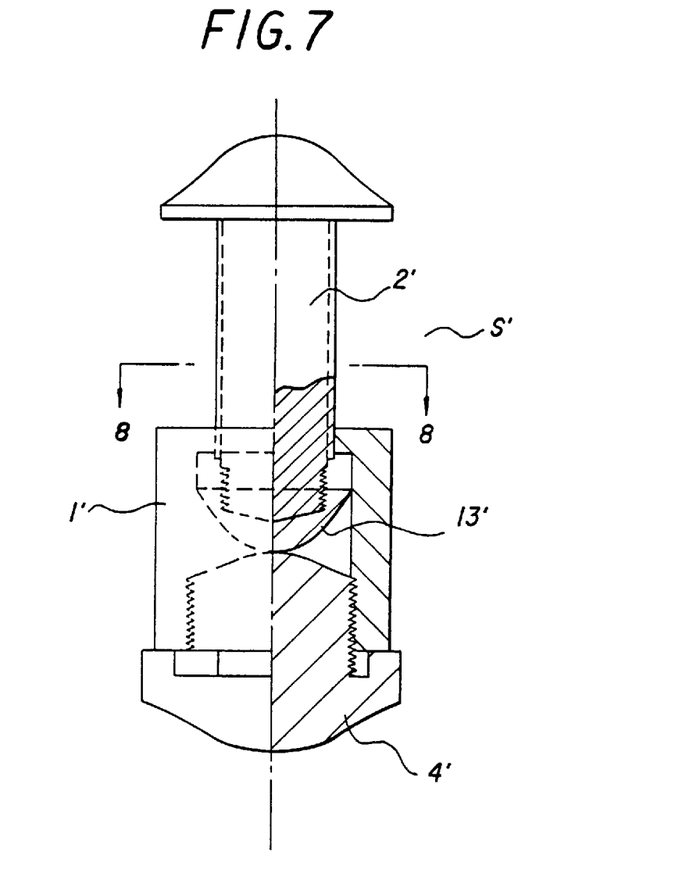
FIG. 7 is a vertical cross-sectional view of a second embodiment of the dental implant of the present invention, where the implant is for an upper jaw.
Figure 8:
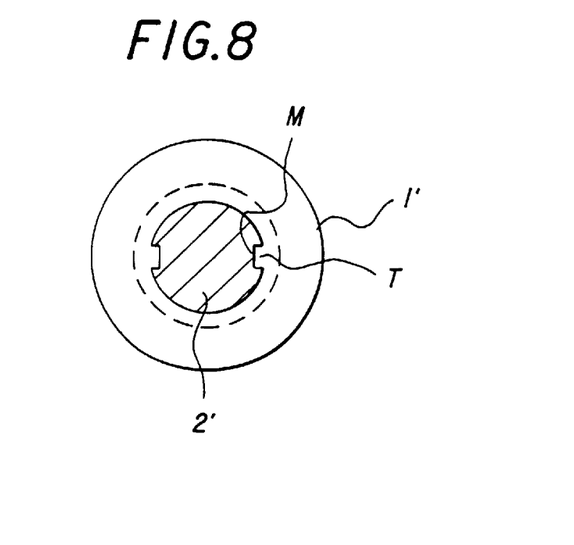
FIG. 8 is a cross-sectional view of the second embodiment of the dental implant of the present invention taken along line X—X of FIG. 7.

FIGS. 7 and 8 illustrate an embodiment of the dental implant according to the present invention which is for embedment into a maxilla. The dental implant illustrated in FIGS. 7 and 8 is different from the dental implant illustrated in FIGS. 1–6 in that the exterior member 1' and middle member 2' of the implant S' are slidably connected. Two grooves M are provided symmetrically on the lateral side of the middle member 2' so as to be parallel with the axis along which there is sliding engagement of the grooves M with protrusions T provided on the inward flange 5' of the exterior member 1'. An end member 13' is screwed into the extremity of the middle member 2'. The end member 13' is attached, for positioning, to the healing cap 4' screwed into the extremity of the exterior member 1'. The projected length of the middle member 2' can be freely adjusted by changing the screwed depth of the healing cap 4' with respect to the exterior member 1'. The adjustment of the middle member 2' is done by sliding the middle member 2' on the exterior member 1'. It should be understood that this invention is not limited to these embodiments, but that the connected length of the middle and exterior members 2', 1' is adjustable is the common thread to all of the embodiments.

Figure 9:
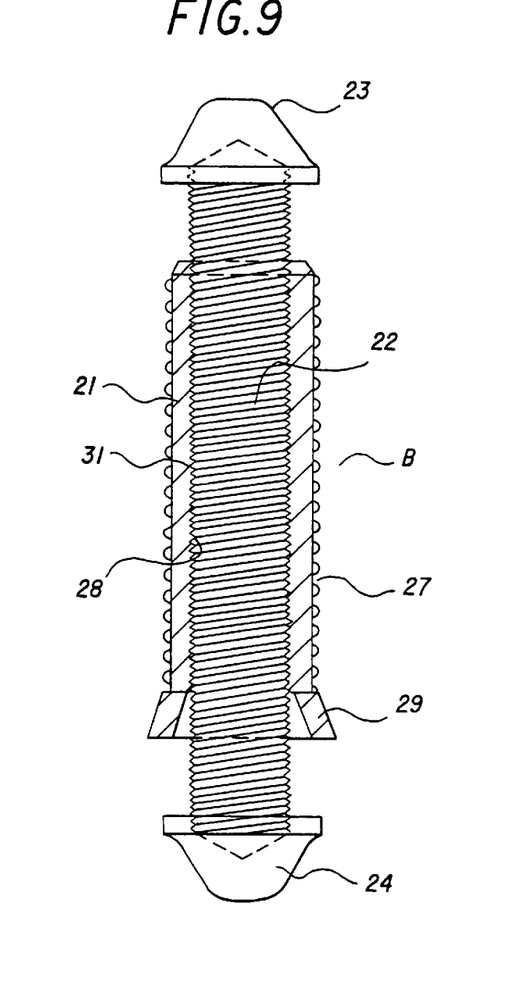
FIG. 9 is a vertical cross-sectional view of a third embodiment of the dental implant of the present invention, showing the fixture part for a lower jaw.
Figure 10:
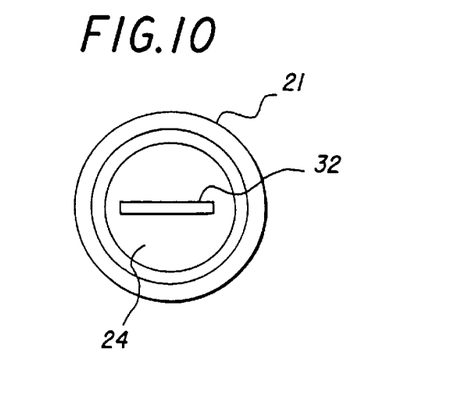
FIG. 10 is a bottom view of the implant of FIG. 9.

FIGS. 9 and 10 represent an embodiment of the implant B for a mandible. The implant B includes an exterior member 21, a middle member 22, a healing cap 23 and an end member 24. The exterior member 21 is a cylinder which is open at upper and lower portions thereof. Fine-pitch female screws 28 and rough-pitched male screws 27 are provided on the inner and outer circumferences of the exterior member 21, respectively. The lowermost portion of the exterior member 21 is provided with a flare guide 29.

Figure 17:
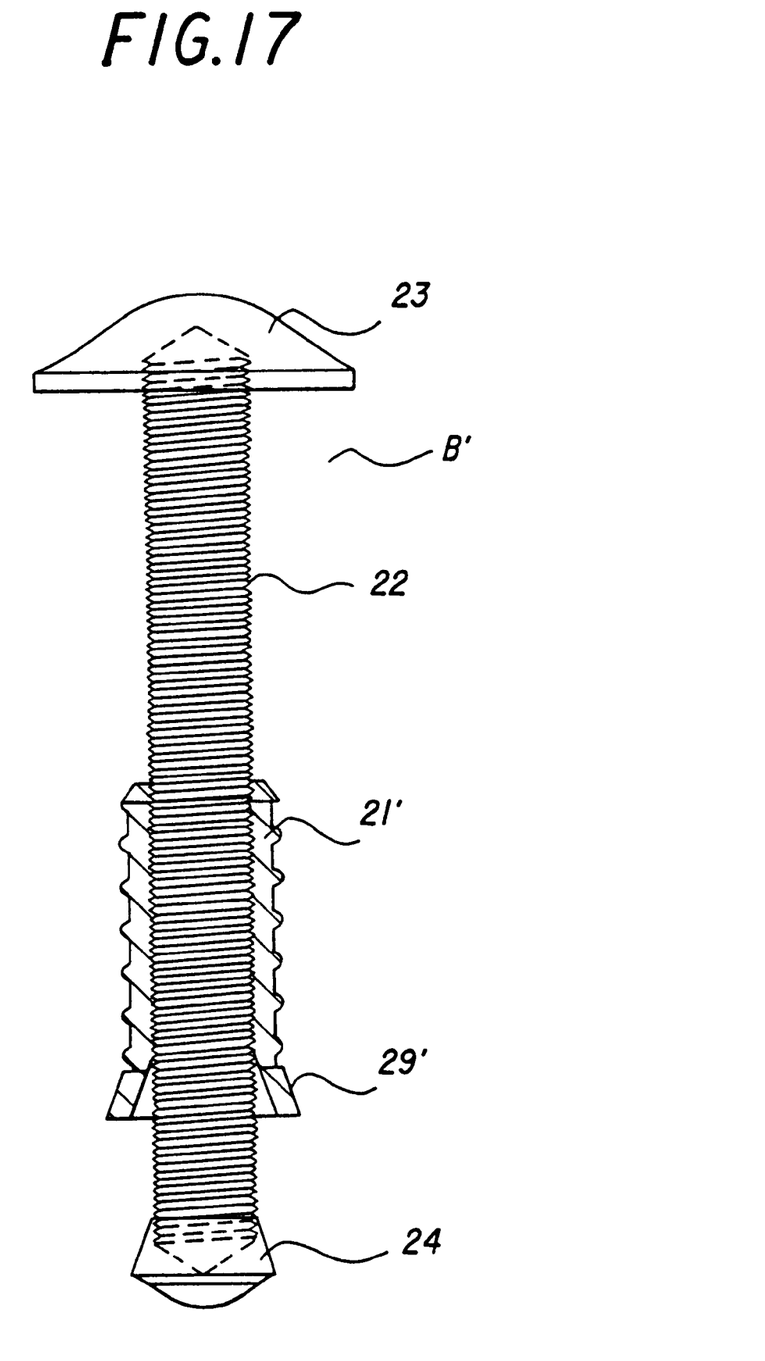
FIG. 17 is a vertical cross-sectional view of a fourth embodiment of the dental implant of the present invention wherein the implant is for a lower jaw.

The middle member 22 is rod-shaped and has on the outer circumference thereof a male thread 31 screwed into the female screw 28 of the exterior member 21. The healing cap 23 and the end member 24 are screwed into the uppermost and lowermost portions of the middle member 22, respectively. The geometrical shape of the healing cap 23 is similar to the geometrical shape of the end member 24 of the implant S. A groove 32 for engagement with a flat or cruciform screwdriver is formed on the end member 24. FIG. 17 illustrates an implant B' for a mandible with the implant B' having a little different exterior member 21'.

Figure 11:
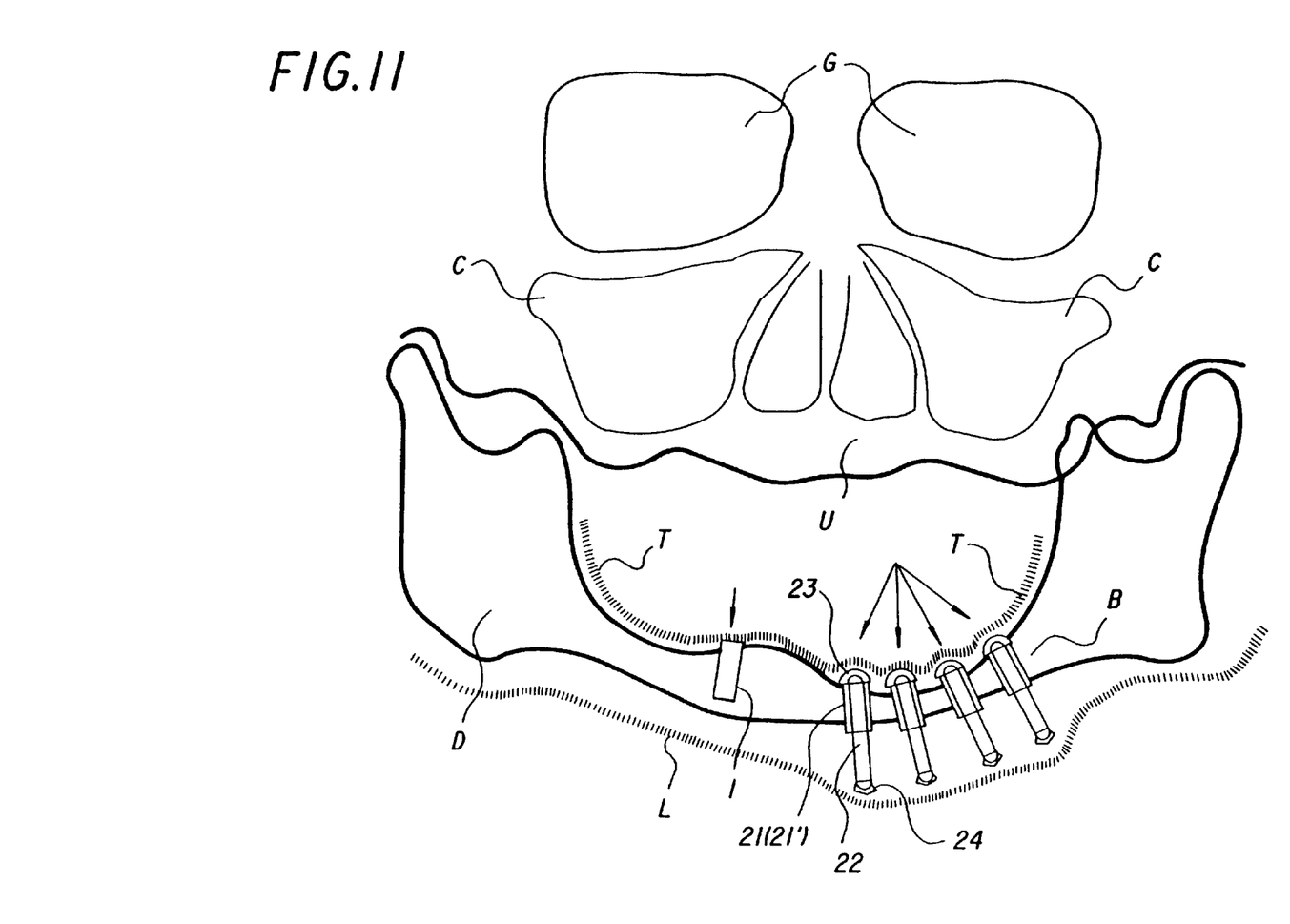
FIG. 11 is a schematic of a human skull showing the dental implants for an lower jaw of the third embodiment just after an operation or surgery in which the implants were embedded into the patient's mandible.

Referring to FIG. 11, the exterior member 21 (21') of the implant B (B') is screwed into the middle member 22 and embedded into jaw bone D. To accomplish the embedment of the exterior member 21 (21') into jaw bone D, the middle member 22 has been screwed into the exterior member 21 (21') to the extent that the healing cap 23 as close as possible to the uppermost portion of the exterior member 21 (21'). Just after the embedment of the exterior member 21 (21') into jaw bone D, the healing cap 23 more or less holds up the mucous membrane T in the oral cavity, while the end member 24, mounted on the lowermost portion of the middle member 22, holds down the skin L under the jaw. The middle member 22 thus positioned just under the skin L can be palpated (i.e., examined by touch). The implant B will be observed in this state for a suitable period of time such as for about two weeks.

Figure 12:
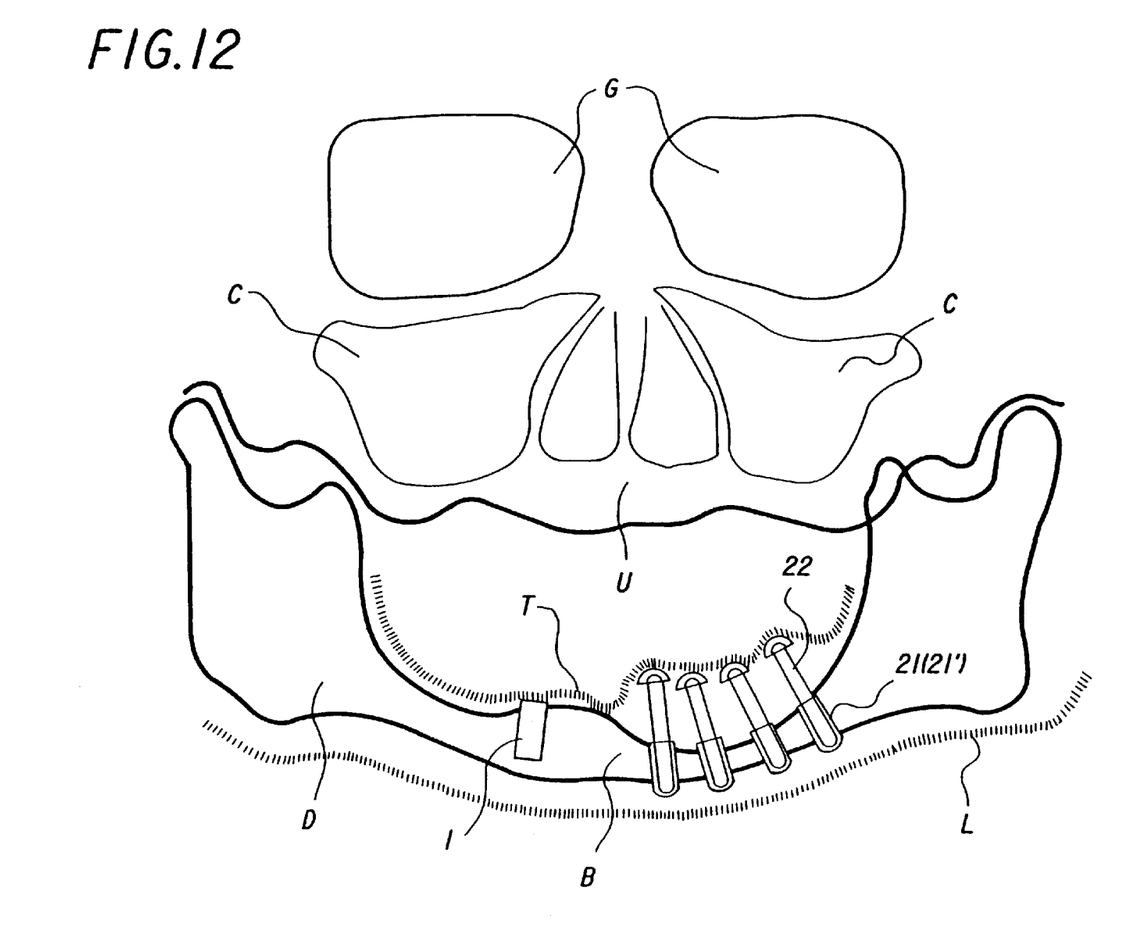
FIG. 12 is a schematic of a human skull illustrating how the same dental implants as in FIG. 11 would look one month after the operation or surgery.

After the observation period has elapsed, the middle member 22 is screwed in daily little by little, for example, by about 2 mm each day. FIG. 12 depicts the state of the middle member 22 one month after the operation or surgery to embed the implant B. In about two weeks, the middle member 22 is pierced through into the oral cavity from just under the skin to expand the mucous membrane T of the oral cavity. The implant is observed in this state for a suitable period of time, such as for about six months.

Figure 13:
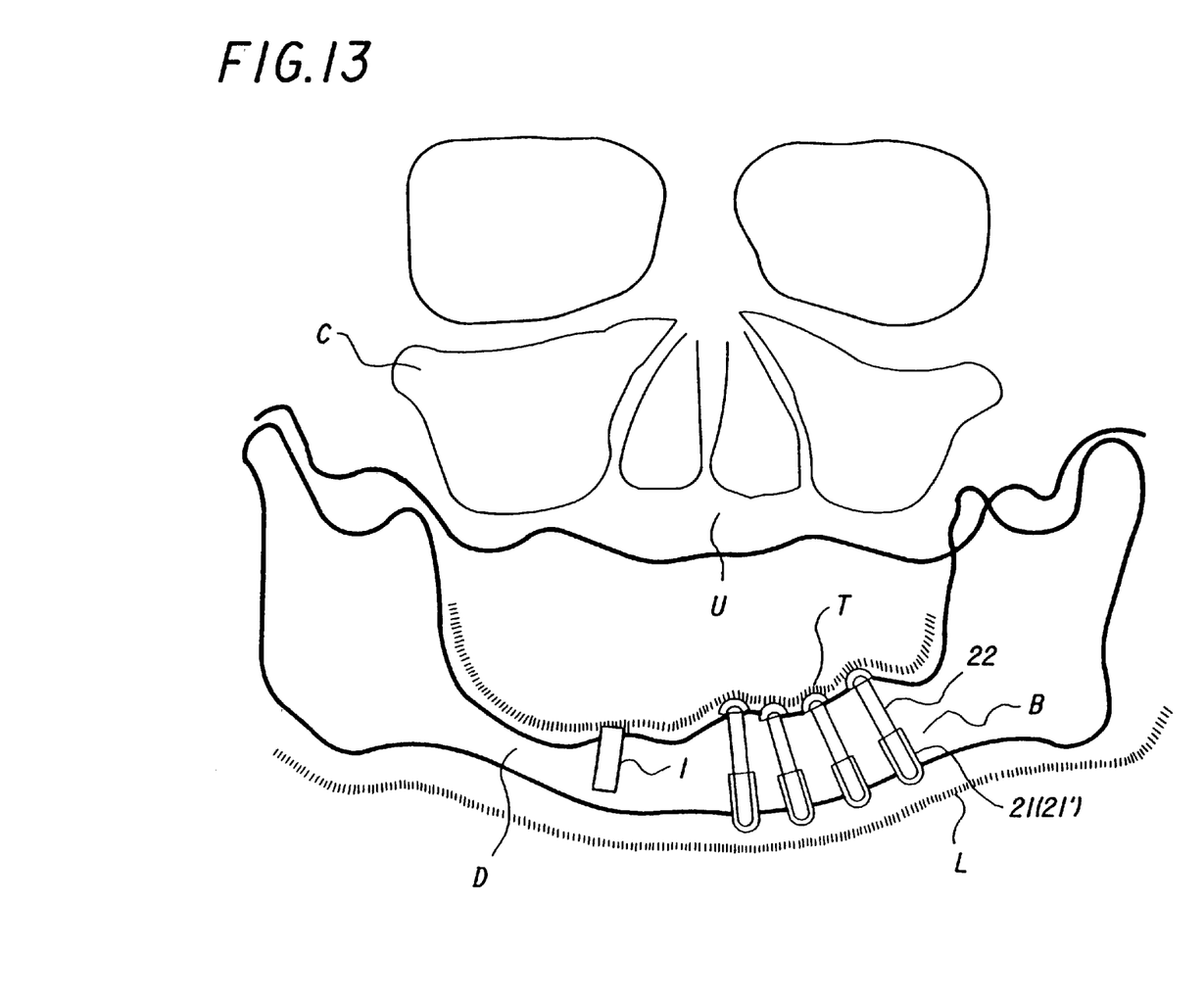
FIG. 13 is a schematic of a human skull illustrating how the same dental implants as in FIG. 11 would look six months after the operation or surgery.

FIG. 13 represents the state of the implants B six months after the operation or surgery in which the implants B were embedded, wherein newly generated bone is observed around the implant B.

Figure 14:
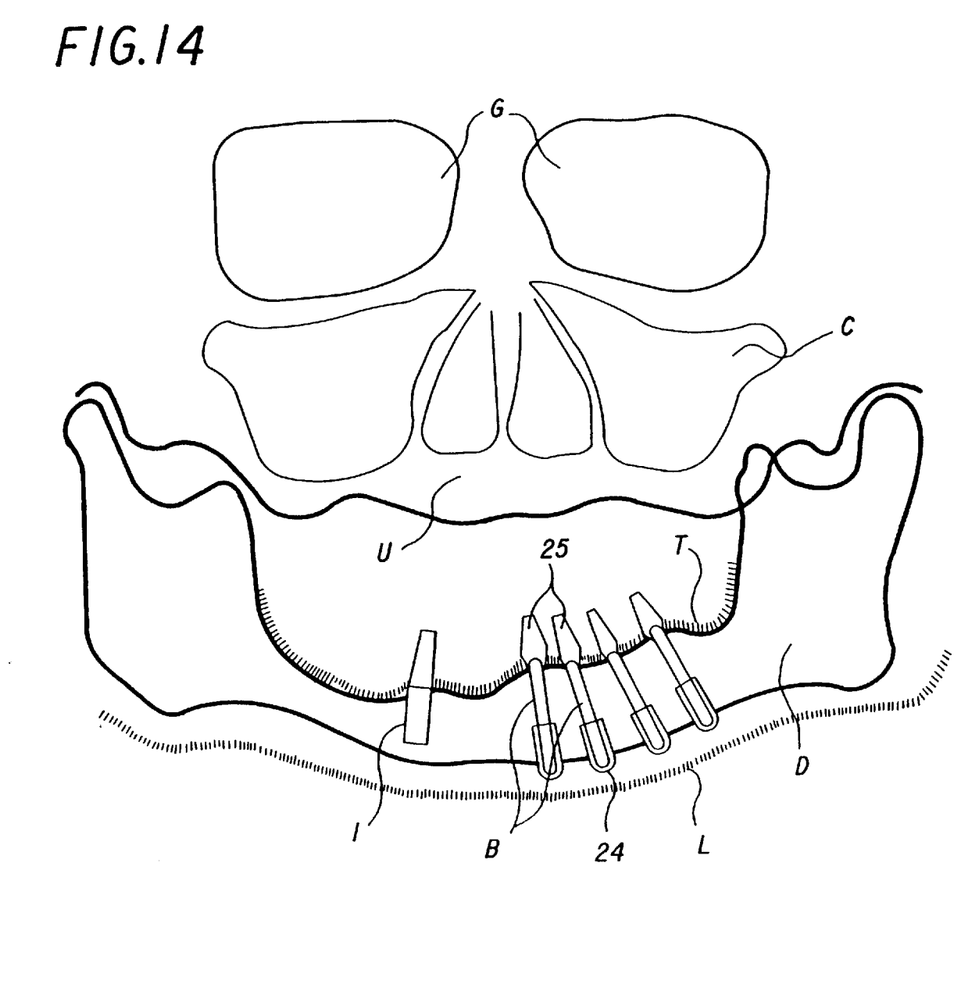
FIG. 14 is a schematic of a human skull illustrating the same dental implants as in FIG. 11 having an abutment mounted thereon.

FIG. 14 illustrates the implant B firmly held by the bone generated around the implant B, where the healing cap 23 has been removed and the abutment 25 is mounted to protrude into the oral cavity outside the mucous membrane T. Dentures, cast crowns and similar can be mounted on this abutment 25.

The implant B for a lower jaw only needs manipulation from inside the oral cavity at the initial operation without any incision through the skin L. Even the secondary operation requires only an extremely small skin incision to allow for the turning of the screw intended to apply the continuous stimulating force. As was the case with the implant S for the upper jaw, the middle member 22 plays the role of an anchor in the bone and can have a bicortical structure surrounded by the cortical bone, thus displaying an excellent holding power. Although the figure shows the osteogenesis in the oral cavity, the bone may be generated on the submaxillary edge by inlaying the implant invertedly.

Figure 15:
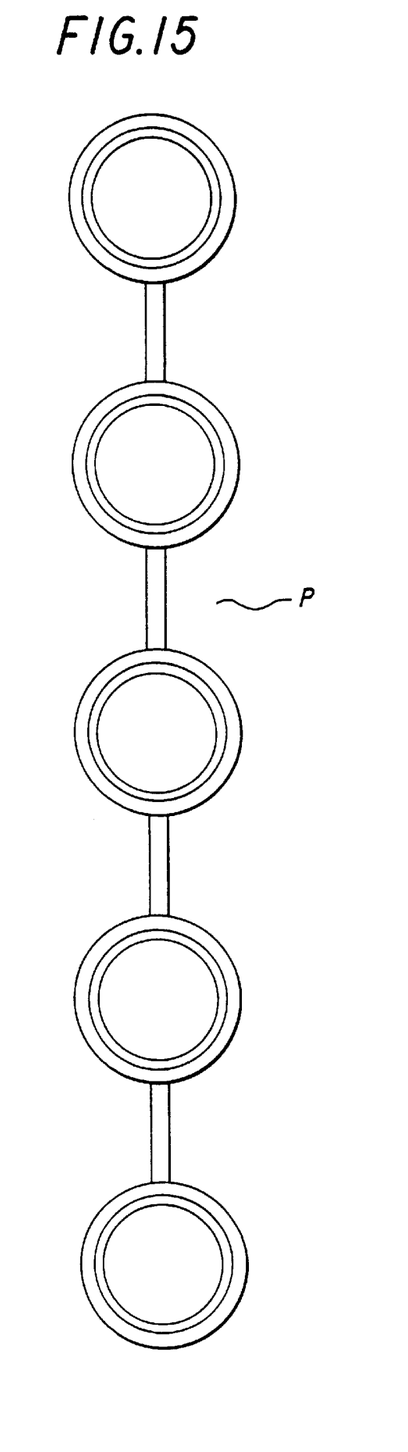
FIG. 15 is a front elevational view of an exterior member connection plate.
Figure 16:
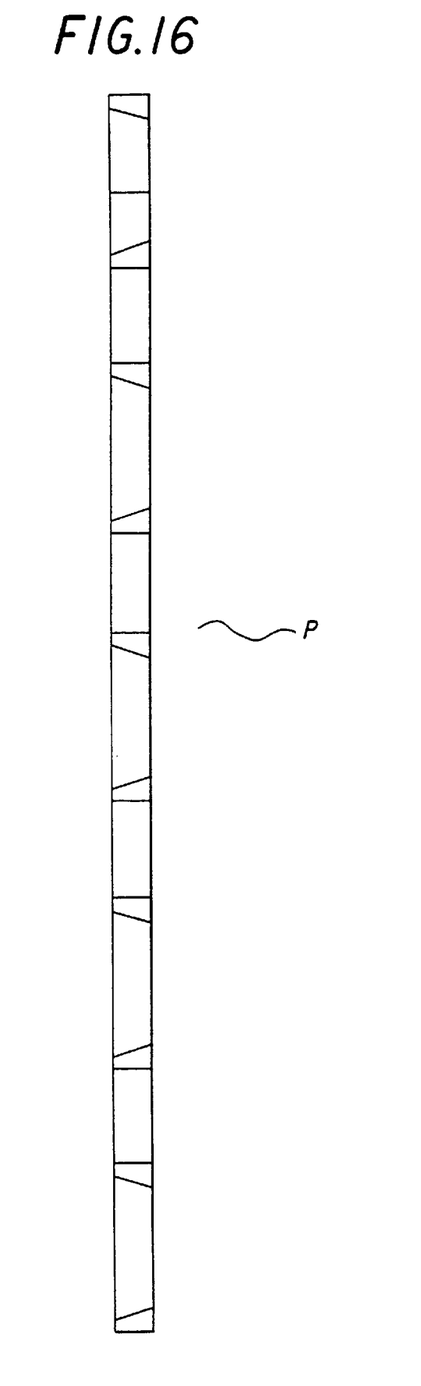
FIG. 16 is a side view of the exterior member connection plate of FIG. 15.

In addition to the implant B for the lower jaw to be embedded from inside the oral cavity, there is another type of implant that necessitates skin incision from the submaxillary edge. We can use, for this latter type, a plate P (Symphysis Plate) that can join respective exterior members as shown in FIGS. 15 and 16.

As the present invention may be embodied in several geometrical forms and dimensions without departing from the spirit of essential characteristics thereof, the present embodiments are therefore illustrative and not restrictive. Although the figures show the external and middle members connected with screws so that their length may be variable, it is possible to adopt other types of structure that allow to the adjustment of their length adequately. It is also possible to adopt triple or higher construction in place of the illustrated double structure of external and middle members.

The material of the implant of the present invention may be some material which is not harmful to the human body and which is excellent in strength, for example, titanium or titanium alloy which is a conventionally known implant material.

The dental implant according to the present invention may be industrially manufactured from titanium, titanium alloy, or other metals by conventionally known processing techniques to be used as a fixing member for dental protheses or cast crowns.

I claim:

1. A dental implant comprising: a fixture part for embedding into any one of a maxilla and a mandible of a patient, wherein said fixture part is composed of a plurality of members, said plurality of members comprising:

a first member, adapted to lift a mucus membrane, including an uppermost member, a middle member, and an end member, wherein said uppermost member is connected to a first end of said middle member, said end member is connected to a second, opposed end of said middle member, and said middle member is cylindrical with an outer circumferential periphery having cooperating means; and a second member being a hollow cylinder, having a hollow throughout and adapted for securement in any one of said maxilla and mandible, having cooperating means for cooperating with said cooperating means of said first member, at a first end thereof, to connect said second member to said first member, wherein said cooperating means of said first member and said cooperating means of said second member cooperate to movably connect said first member to said second member in a manner so that a length of said fixture part is variable through the hollow of said calinder from the side opposite a mucus membrane in order for said fixture part to be extended to lift up a mucous membrane on a surface of bone of any one of said maxilla and said mandible.

2. The dental implant as claimed in claim 1, wherein said cooperating means of said second member are female screws and said cooperating means of said first member are male screws formed in an outer periphery of said middle member so that said female screws mate with said male screws in order for said second member and said first member to be movably connected to each other.

3. The dental implant of claim 1, wherein said end member of said first member is housed within an interior of said hollow cylinder of said second member.

4. A dental implant comprising: a fixture part for embedding into any one of a maxilla and a mandible of a patient, wherein said fixture part is composed of a plurality of members, said plurality of members comprising:

a first member including an uppermost member, a middle member, and an end member, wherein said uppermost member is connected to a first end of said middle member, said end member is connected to a second, opposed end of said middle member, and said middle member is cylindrical with an outer circumferential periphery having cooperating means;

a second member being a hollow cylinder having cooperating means for cooperating with said cooperating means of said first member, at a first end thereof, to connect said second member to said first member, wherein said cooperating means of said first member and said cooperating means of said second member cooperate to movably connect said first member to said second member in a manner so that a length of said fixture part is variable in order for said fixture part to be extended to lift up a mucous membrane on a surface of bone of any one of said maxilla and said mandible; and wherein said cooperating means of said second member are protrusions protruding radially inwardly from an inner wall of said second member and said cooperating means of said first member are grooves formed in an outer periphery of said middle member so that said protrusions mate with said grooves in order for said second member and said first member to be axially slidable on each other.

5. A dental implant comprising: a fixture part for embedding into any one of a maxilla and a mandible of a patient, wherein said fixture part is composed of a plurality of members, said plurality of members comprising:

a first member including an uppermost member, a middle member, and an end member, wherein said uppermost member is connected to a first end of said middle member, said end member is connected to a second, opposed end of said middle member, and said middle member is cylindrical with an outer circumferential periphery having cooperating means;

a second member being a hollow cylinder having cooperating means for cooperating with said cooperating means of said first member, at a first end thereof, to connect said second member to said first member, wherein said cooperating means of said first member and said cooperating means of said second member cooperate to movably connect said first member to said second member in a manner so that a length of said fixture part is variable in order for said fixture part to be extended to lift up a mucous membrane on a surface of bone of any one of said maxilla and said mandible; and any one of an abutment part and a healing cap which is attached to a second end of said second member.

6. A dental implant comprising: a fixture part for embedding into any one of a maxilla and a mandible of a patient, wherein said fixture part is composed of a plurality of members, said plurality of members comprising:

a first member including an uppermost member, a middle member, and an end member, wherein said uppermost member is connected to a first end of said middle member, said end member is connected to a second, opposed end of said middle member, and said middle member is cylindrical with an outer circumferential periphery having cooperating means;

a second member being a hollow cylinder having cooperating means for cooperating with said cooperating means of said first member, at a first end thereof, to connect said second member to said first member, wherein said cooperating means of said first member and said cooperating means of said second member cooperate to movably connect said first member to said second member in a manner so that a length of said fixture part is variable in order for said fixture part to be extended to lift up a mucous membrane on a surface of bone of any one of said maxilla and said mandible; and wherein a second end of said second member includes a hexagonal nut.

7. A dental implant comprising: a fixture part for embedding into any one of a maxilla and a mandible of a patient, wherein said fixture part is composed of a plurality of members, said plurality of members comprising:

a first member including an uppermost member, a middle member, and an end member, wherein said uppermost member is connected to a first end of said middle member, said end member is connected to a second, opposed end of said middle member, and said middle member is cylindrical with an outer circumferential periphery having cooperating means;

a second member being a hollow cylinder having cooperating means for cooperating with said cooperating means of said first member, at a first end thereof, to connect said second member to said first member, wherein said cooperating means of said first member and said cooperating means of said second member cooperate to movably connect said first member to said second member in a manner so that a length of said fixture part is variable in order for said fixture part to be extended to lift up a mucous membrane on a surface of bone of any one of said maxilla and said mandible; and wherein said end member at said second end of said first member includes a groove therein for engagement with a screwdriver.

8. A dental implant comprising: a fixture part for embedding into any one of a maxilla and a mandible of a patient, wherein said fixture part is composed of a plurality of members, said plurality of members comprising:

a first member including an uppermost member, a middle member, and an end member, wherein said uppermost member is connected to a first end of said middle member, said end member is connected to a second, opposed end of said middle member, and said middle member is cylindrical with an outer circumferential periphery having cooperating means;

a second member being a hollow cylinder having cooperating means for cooperating with said cooperating means of said first member, at a first end thereof, to connect said second member to said first member, wherein said cooperating means of said first member and said cooperating means of said second member cooperate to movably connect said first member to said second member in a manner so that a length of said fixture part is variable in order for said fixture part to be extended to lift up a mucous membrane on a surface of bone of any one of said maxilla and said mandible; and a flared guide at a second end of said second member which flairs radially outwardly from an outer periphery of said second member.

9. The dental implant of claim 8, wherein said cooperating means of said second member are female screws in an inner circumferential periphery of said second member, with said female screws being fine-pitched, and said cooperating means of said second member are male screws on an outer circumferential periphery of said middle member of said first member, with said male screws being fine-pitched.

10. The dental implant of claim 9, wherein an outer circumferential periphery of said second member having male screws which are rough-pitched.

11. A dental implant comprising: a fixture part for embedding into any one of a maxilla and a mandible of a patient, wherein said fixture part is composed of a plurality of members, said plurality of members comprising:

a first member including an uppermost member, a middle member, and an end member, wherein said uppermost member is connected to a first end of said middle member, said end member is connected to a second, opposed end of said middle member, and said middle member is cylindrical with an outer circumferential periphery having cooperating means;

a second member being a hollow cylinder having cooperating means for cooperating with said cooperating means of said first member, at a first end thereof, to connect said second member to said first member, wherein said cooperating means of said first member and said cooperating means of said second member cooperate to movably connect said first member to said second member in a manner so that a length of said fixture part is variable in order for said fixture part to be extended to lift up a mucous membrane on a surface of bone of any one of said maxilla and said mandible; and wherein said second member includes an inwardly projecting flange at said first end thereof and said inwardly projecting flange includes an inwardly facing wall which includes said cooperating means which are female screws which mate with said cooperating means of said middle member of said first member which are male screws.

12. The dental implant of claim 11, wherein an inner diameter at said first end of said second member is smaller than an inner diameter at a second end of said second member.

* * * * *